United States Patent [19]

Makin et al.

[11] 4,255,591

[45] Mar. 10, 1981

[54] CARBONYLATION PROCESS

[75] Inventors: Earle C. Makin, Dickinson; Jerry L. Price, Texas City; Yu W. Wei, Houston, all of Tex.

[73] Assignee: Monsanto Company, St. Louis, Mo.

[21] Appl. No.: 962,458

[22] Filed: Nov. 20, 1978

[51] Int. Cl.³ .................. C07C 51/10; C07C 51/12; C07C 51/14; C07C 67/36; C07C 67/37; C07C 67/38

[52] U.S. Cl. .................................. 562/517; 55/16; 260/410.9 R; 260/413; 260/428; 260/546; 260/549; 560/78; 560/79; 560/97; 560/105; 560/106; 560/114; 560/175; 560/191; 560/204; 560/207; 560/218; 560/232; 560/233; 560/248; 562/406; 562/494; 562/497; 562/519; 562/520; 562/522; 562/593; 562/608

[58] Field of Search ........... 562/519, 520, 521, 522, 562/497, 406, 517, 608; 560/97, 114, 105, 175, 204, 106, 206, 232, 207, 233, 248; 260/546, 549, 428, 410.9 R, 413; 55/16

[56] References Cited

U.S. PATENT DOCUMENTS 3,845,121 10/1974 Eubanks et al. .................. 562/519
4,102,922 7/1978 Price ................................. 560/232

OTHER PUBLICATIONS

Chem. Engineering Progress, pp. 76–78, Oct. 1977.

*Primary Examiner*—Vivian Garner
*Attorney, Agent, or Firm*—Thomas B. Leslie

[57] ABSTRACT

There is provided an improved continuous homogeneous catalytic carbonylation process wherein a mixed gas stream is removed from the carbonylation reactor, condensable liquids separated from said gas stream and said gas stream vented, the improvement comprising contacting said gas stream with a plurality of hollow fiber membranes selectively permeable to hydrogen under conditions substantially non-degrading of the membranes to generate a non-permeated gas stream of higher carbon monoxide content and recycling said non-permeated gas stream to the carbonylation process reactor. There is also provided for the recovery and recycle to the process of carbonylation products such as acetic or propionic acids by adsorption and removal from a solid adsorbent or absorption in a liquid absorbent.

30 Claims, No Drawings

CARBONYLATION PROCESS

The present invention relates to an improved carbonylation process. More particularly this invention relates to such a process wherein at least a portion of unreacted carbon monoxide gas is recovered for reuse.

In recent years processes for producing carboxylic acids and esters by carbonylating olefins, alcohols and ester, ether or halide derivatives of alcohols in the presence of homogeneous catalyst systems containing a rhodium or iridium component and an iodine or bromine component have been introduced into commercial operation. These carbonylation processes have proved to be distinct improvements over carbonylation processes of the earlier prior art.

In the carbonylation of alcohols, olefins and alcohol derivatives by carbon monoxide under the influence of these recently developed homogeneous catalysts an accompanying reaction involves a water gas shift of any water present to produce hydrogen and carbon dioxide. Since the catalytic carbonylation is promoted by the presence of some water in the reaction, water is generally present. The hydrogen and carbon dioxide gases generated by the accompanying shift reaction, however, lower the partial pressure of the carbon monoxide available for the continuous catalytic carbonylation reaction. Hence, in a continuous process a venting of the vapor-filled portion of the carbonylation reactor is required to prevent the buildup of such hydrogen and carbon dioxide gases within the reactor. The quantity of such gas vented must be limited, however, since the vapor in the reactor is predominantly unreacted carbon monoxide gas and substantial losses of reactant carbon monoxide would rapidly become excessive and economically unsupportable. Thus, a means to recover the carbon monoxide reactant being lost would be highly desirable.

Previously known methods for recovery of carbon monoxide gas are not suitable for use with the carbonylation process vented gas mixtures. Generally this has been true because the vented gas mixtures contain corrosive inclusions of carboxylic acid or anhydride products and/or alkyl halides present in the reactor as a result of the halide component promoters for the catalyst system. In other instances the recovery of carbon monoxide is accompanied by recovery of undesired carbon dioxide gas which is an inert diluent in the carbonylation reaction. Even when provision is made in the carbonylation processes for recovery of substantial portions of the carbonylation products and alkyl halides there still generally remain amounts in vapor form which, although insufficient to recover, still render the vented gas stream unsuitable for treatment by most gas recovery means.

Surprisingly it has now been found that a large portion of previously lost carbon monoxide reactant can be recovered, the efficiency of the carbonylation reaction improved and additional carbonylation product yield realized by the improved process of the present invention.

The present invention is an improvement in a continuous homogeneous catalytic carbonylation process wherein a mixed gas stream is removed from the vapor containing portion of the carbonylation reactor, condensable liquids separated from said gas stream, and said gas stream vented, wherein the improvement comprises contacting said vent gas stream with a plurality of hollow fiber membranes selectively permeable to hydrogen under conditions substantially non-degrading of the membranes to generate a non-permeated gas stream of higher carbon monoxide content than the said vent gas stream and a permeated gas stream lower in carbon monoxide content than said vent gas stream and recycling said non-permeated gas stream of increased carbon monoxide content to the said carbonylation process reactor. Generally the process of the present invention is operated in such a manner that it would result not only in the recovery of a portion of the unreacted carbon monoxide gas normally lost through venting but will also recover carbonylation product normally lost as vented vapor and recycling of such recovered product to said carbonylation process.

As a result of this improved process, a large portion of the previously lost carbon monoxide reactant can be recovered. Likewise the efficiency of the carbonylation reaction based upon the amount of carbon monoxide reactant charged is improved. Furthermore, additional carbonylation product yield is usually realized through recovery of portions of such product normally lost through venting.

DESCRIPTION OF THE PREFERRED EMBODIMENTS

The present invention is directed to those continuous homogeneous catalytic carbonylation processes wherein olefins, alcohols and ester, halide and ether derivatives of the alcohols are reacted with carbon monoxide in a liquid phase system in the presence of a homogeneous catalyst system that contains a rhodium or iridium component and an iodine or bromine component. These homogeneous catalytic carbonylation processes and the homogeneous catalyst employed therein have been extensively described in the patent literature. Consequently a detailed description of the carbonylation reaction and of the several processes for recovery of liquid carbonylation products is not set forth herein. For a detailed description of the carbonylation reaction and the homogeneous catalyst employed therein reference may be made to U.S. Pat. No. 3,845,121 of Eubanks et al, issued Oct. 29, 1974.

In such homogeneous catalytic carbonylation processes the presence of water in the reaction results in the formation of hydrogen and carbon dioxide gases which, if not removed from the vapor section of the reactor, would serve to dilute the partial pressure of the carbon monoxide reactant and decrease the efficiency of the carbonylation reaction. Thus, a vent of the gases collected in the vapor portion of the reactor is required.

Generally in such catalytic carbonylation processes the stream of vented gases removed from the reactor at reaction temperature is cooled by heat exchange with a cooling medium in order to condense any condensable liquids present as vapors in the mixed gas stream and thereafter the condensed liquids are separated from the gas stream. In this manner there are generally removed from the vent gas stream such normally liquid components present as methanol, water, carboxylic acid esters and practically all of any carboxylic acid carbonylation product and alkyl halide present in such gas stream. Those amounts of the carbonylation product and alkyl halide still present in vapor form are sufficient, however, to pose problems in the further treatment of vent gas streams. Hence, the normal practice has been to either vent or flare this gas stream.

In some instances it has been found desirable to scrub the resulting vented gas stream after separation of condensable liquids therefrom with a portion of the crude carbonylation product. This scrubbing treatment is designed to remove substantially all of the remaining alkyl halide present in the vent gas stream and to recover same by absorption into the crude carbonylation product. Traces of carboxylic acid esters are likewise absorbed into the crude carbonylation product scrubbing liquid. This treatment, however, also results in saturating the vent gas stream thus treated with carbonylation product. In some instances it does not remove the final traces of alkyl halide present. The vent gas stream is thus still contaminated in such a way that it has not generally been considered suitable for further use and, as noted above, this stream has normally been vented or flared. As such, the loss of carbon monoxide reactant comprising the major proportion, commonly 65 to 80%, of such vent gas stream represents loss of valuable reactant and decrease in overall efficiency of the carbonylation process.

By employment of the present invention it has now been found possible to recover much of this previously lost carbon monoxide reactant and thus increase the efficiency of the catalytic carbonylation processes. In the most preferred alternatives the yield of carbonylation products is also increased.

The prevent invention involves contacting of the vent gas stream with hollow fiber semi-permeable membranes selectively permeable to hydrogen in order to produce a non-permeated portion of the vent gas considerably enriched in carbon monoxide content and recycling such non-permeated gas stream to the carbonylation process reactor. In order to carry out a practical industrial process the contacting of the vent gas stream with the semi-permeable membranes must be under conditions which will result in minimal degradation of the membranes, referred to herein as "conditions substantially non-degrading of the membranes".

By "conditions substantially non-degrading of the membranes" there is meant that conditions of contact of the vent gas with the membranes will result in no sudden or relatively short-term major changes in the condition or permeability characteristics of the membranes. Thus, the type of membrane degradation which is to be avoided is that which takes place relatively suddenly, over a period of a few hours or a very few days and is relatively massive in character, i.e. a change in permeability to one or more gases of the order of 50% or greater. There is not embraced by the above term such very gradual changes over a prolonged period of several weeks to several months and of more minor nature in the permeability of the hollow fiber membranes to one or more gases of the order of 20% or less. Such more minor and very gradual changes are commonly encountered in the use of semi-permeable membranes with many systems of gases and are not to be deemed embraced by the term "conditions substantially non-degrading of the membranes".

Such non-degrading conditions can be realized in several different ways depending upon the nature of the semi-permeable hollow fiber membranes employed. Thus, if hollow fiber membranes are fabricated from metallic foil such as palladium or palladium alloy foils, or from such inorganic materials as glass, silica or alumina the membranes would not be degraded by the presence of carbonylation products or alkyl halides in the vent gas streams permeated therethrough. In the present invention, however, such metal or inorganic hollow fiber membranes are not the membranes of choice. Metal foils, such as the palladium or palladium alloy foils, permeate only hydrogen and exclude all other gases. They are also relatively slow in the rate of permeation to hydrogen except at extreme temperature conditions. Consequently, none of the carbon dioxide gas generated in the carbonylation processes would be permeated and removed from the system by such membranes. The inorganic membranes on the other hand are generally not sufficiently selective as between hydrogen and carbon monoxide to constitute the preferred membranes for use. Such metal and inorganic semi-permeable membranes do satisfy, however, the requirements for contact under conditions non-degrading of the membranes.

Certain organic polymeric semi-permeable membranes are likewise highly resistant to degradative attack by relatively very small amounts of carbonylation products such as acetic acid and such membranes as polyacrylonitrile and polyolefins such as polyethylene or polypropylene also fulfill the requirement of contact under conditions non-degrading of the membranes. Such membranes are likewise not membranes of choice because of their relatively slow rates of permeation of hydrogen and others of the light gases.

The great majority of organic polymeric semi-permeable membranes including those demonstrating relatively high rates of permeation and selectivity of hydrogen as compared to other gases commonly demonstrate a potential for degradation by such carbonylation products as acetic and propionic acid. In order that the requirement for conditions substantially non-degrading of the membranes be met when employing such organic polymeric membranes the removal of the remaining amounts of carbonylation products and traces of alkyl halides, if any, from the vent gas streams are required.

The removal of such inclusions in the vent gas stream can be accomplished in several different ways. As pointed out above, it has generally been found desirable to scrub a vented mixed gas stream with a portion of the crude liquid carbonylation product in order to absorb and recover into such crude product any alkyl halides present so that those halides would not be lost from the continuous process. Such generally desirable treatment, however, results in saturating the thus scrubbed vent gas with carbonylation product in vapor form and sometimes leaves traces of alkyl halide vapors in the vent gas. In the instance of acetic or propionic acids as such carbonylation product, this treatment step renders the vent gas potentially corrosive and degradative of organic polymeric hollow fiber membranes desired for use in the present process. Among suitable treatments to remove such carbonylation products and alkyl halides, if present in the vent gas, are adsorption upon solid adsorbents such as activated carbon, silica, alumina, bauxite, etc., and also absorption into liquid absorbents such as alkanols, i.e. methanol or ethanol, and water. Such absorption or adsorption treatments frequently offer the potential for recovery of additional carbonylation product, increasing the yield thereof and further increasing the efficiency of the overall carbonylation processes.

Among the most desirable of the homogeneous carbonylation processes for the incorporation of the present invention are those for the production of acetic acid in which the major reactants are methanol and carbon monoxide and propionic acid in which the major reactants are ethylene and carbon monoxide. Carbonylation processes for the production of other carboxylic acids, anhydrides and esters also frequently require venting or removal of such mixed gas streams from the reactor and in such processes the present invention is likewise useful. In the remaining description the use of the present invention will be illustrated in connection with the vent gas generated in a process for the production of acetic acid by homogeneous catalytic carbonylation reaction.

In a typical homogeneous catalytic carbonylation process for the production of acetic acid the mixed gas vented from the reactor is comprised principally of carbon monoxide, hydrogen, carbon dioxide and nitrogen as well as methyl halide, either iodide or bromide, water and acetic acid as well as traces of methyl acetate, methanol and methane. After cooling and condensing the condensable liquids in the vent gas stream such liquids are separated for return to the process. Thereafter the composition of the remaining vent gas will generally range from about 65 to 80% carbon monoxide, 10 to 20% hydrogen and smaller amounts of carbon dioxide, nitrogen and methyl halide with only traces of methane, acetic acid, methyl acetate and water remaining in vapor form. Upon the scrubbing of the remaining vent gas stream with crude acetic acid product the traces of methyl halide and methyl acetate are generally eliminated and the water reduced to a trace, but the vent gas is then saturated at its ambient temperature with the acetic acid employed for scrubbing. In order that the vent gas can be treated under conditions for non-degradation of most organic polymeric membranes such acetic acid must be removed from the remaining vent gas stream.

One preferred alternative for the removal of the acetic acid and any traces of methyl halide present in vapor form involves adsorbing such acetic acid vapor onto solid adsorbents such as activated charcoal, silica, alumina, or bauxite. This is conveniently accomplished by passage of the vent gases through a vessel containing a bed of the solid adsorbent. In the event the vent gas line is long or encounters ambient temperatures it is often desirable to include a liquid trap before passing the vent gas to the bed of solid adsorbent. In a typical continuous process a plurality of such solid adsorbent beds are arranged in parallel so that while the vent gas stream is being treated in one such bed, one or more other beds is undergoing regeneration preparatory to use. From the solid adsorbent bed the vent gas is passed into contact with hollow fiber permeable membranes. Most organic polymeric semi-permeable membranes selectively permeable to hydrogen are likewise somewhat more permeable to carbon dioxide than to the other gases present in the vent gas stream. Therefore permeation of a major portion of both the hydrogen and carbon dioxide present in the vent gas to the permeate gas side of the hollow fiber membranes is accomplished. At the same time there remains on the non-permeate side of the hollow fiber membranes a mixed gas stream grossly depleted in hydrogen and carbon dioxide and of substantially higher carbon monoxide content, generally greater than 90 mole percent carbon monoxide. The gas stream from the non-permeate side of the membranes is thus ideally suited for recycle to the carbonylation reaction. This can conveniently take place by compressing the non-permeated gas to substantially the same pressure as the initial carbon monoxide feed to the reaction and blending said gas with such carbon monoxide feed stream. Carbon monoxide thus recovered and recycled to the carbonylation reaction affords improved efficiency of the process based upon the total carbon monoxide charged to the reaction.

The preferred alternative described above also affords potential for improved yield of the acetic acid product. The solid adsorbent can be regenerated by any stream of gas or vapor which will remove the adsorbed acetic acid therefrom. Steam has been found to be suitable regenerating vapor stream. It has been found to be preferable, however, to employ a stream of essentially carbon monoxide gas such as a portion of the carbon monoxide feed or of the recovered non-permeated gas for the purpose of regeneration of the solid adsorbent. In such manner the adsorbed acetic acid which would otherwise be lost to the process is recovered and recycled to the carbonylation reactor along with the compressed carbon monoxide gas stream. If desired such stream can be heated by any convenient means of heat exchange for more rapid removal of the adsorbed acetic acid.

Another preferred alternative for the removal of the acetic acid carbonylation product present in the vent gas as vapor is to treat said vent gas with a liquid absorbent such as an alkanol or water. The most preferred absorbent is an alkanol such as methanol or ethanol, since these liquids can be directly recycled to the carbonylation process together with the absorbed acetic or propionic acids. Water is a suitable liquid absorbent for the removal of the acetic or propionic acid, and a portion of the water absorbent can frequently be recycled to the process. Unless excess distillation capacity is available, however, it is generally found uneconomical to recover a large portion of the very dilute solutions of the acids in water which are generated by the use of water absorbent and such portion is eliminated from the process.

When a liquid absorbent such as an alkanol is employed for the removal of carboxylic acid product the treated gas stream will contain vapors of such alkanol in an amount approaching or equaling saturation at the temperature of the gas stream. The tensile and compressive strengths of certain of the organic polymeric membranes have been found to be sensitive to concentrations of methanol vapor at or near saturation. Thus it is often desirable to reduce the concentration of methanol vapor in such gas streams to minimize such possible strength losses. Several convenient methods for effecting this reduction are available. Among such methods are an additional water scrub, cooling the gas stream and condensing and separating liquified methanol and reheating the gas stream and reducing the pressure of the treated vent gas stream. Frequently a combination of such methods can be used to reduce the concentration of methanol vapor in the gas stream to less than 50% and preferably less than 35% of saturation.

A convenient methanol removal treatment constitutes cooling the vent gas stream by some 30° to 40° C., separating condensed methanol, reheating the gas stream by the same or greater amount, and reducing the pressure thereon by 6 to 7 atmospheres. This will result in removal of methanol from the vent gas stream to a concentration below 35% of saturation, a level at which the sensitivity problem is not apparent.

The vent gas stream after substantial removal of any carboxylic acid product and alkyl halide as described, is contacted with the semi-permeable hollow fiber membranes for separation of a large proportion of the hydrogen and preferably the carbon dioxide present and generation of a more concentrated carbon monoxide non-permeated gas stream for recycle to the carbonylation process. The permeated gas stream produced by permeation through the membranes and comprising chiefly hydrogen and carbon dioxide can be vented, burned or flared as desired. The vent gas stream is contacted with hollow fiber separation membranes which exhibit selectivity to the permeation of hydrogen and preferably carbon dioxide as compared to the permeation of carbon monoxide and other gases present, such as nitrogen. The higher the selectivity of the membrane for the permeation of hydrogen and preferably carbon dioxide as compared to the carbon monoxide the higher will be the concentration of carbon monoxide in the non-permeated gas stream desired for recycle.

Generally the selectivity or separation of a membrane is described in terms of the ratio of the permeability of the fast permeating gas, i.e. hydrogen, to the permeability of the slow permeating gas, i.e. carbon monoxide, wherein the permeability of the gas through the membrane can be defined as the volume of gas at standard temperature and pressure which passes through the membrane per square centimeter of surface area per second for a partial pressure drop of one centimeter of mercury across the membrane per unit thickness. This ratio is referred to as the separation factor of a membrane for the specific gases the permeabilities of which are used. Desirably, the separation factor of the selected membranes for hydrogen over carbon monoxide is at least about 10. Separation factors for hydrogen over carbon monoxide of 50 or 100 or greater may be provided by certain membranes. Desirably, membranes selectively permeable to hydrogen should also possess a separation factor for carbon dioxide over carbon monoxide of from about 2 to about 50, and preferably from about 5 to about 25. Particularly desirable membranes exhibit hydrogen permeabilities of at least $1 \times 10^{-6}$, preferably $1 \times 10^{-5}$ to $1 \times 10^{-4}$ cubic centimeters of hydrogen per square centimeter of membrane surface area per second at a partial pressure drop of one centimeter of mercury across the membrane per unit of thickness. Likewise, particularly desirable membranes for use in this process also exhibit carbon dioxide permeabilities of at least $1 \times 10^{-6}$ and preferably $5 \times 10^{-6}$ to $5 \times 10^{-5}$ cubic centimeters of carbon dioxide per square centimeter of membrane surface area per second at a partial pressure drop of one centimeter of mercury across the membrane per unit of thickness.

Partial pressure differentials of hydrogen and carbon dioxide across the membrane provide the driving force for the permeation of hydrogen and carbon dioxide and depend on the concentrations of hydrogen and carbon dioxide as well as the total pressures on each side of the membrane. The pressure at which the vent gas stream contacts the feed side of the membranes will depend upon the pressure at which the gas stream was removed from the carbonylation reactor, the pressure drop in the line and treating vessels intervening and any adjustment in the pressure which may have been made. Generally, such vent gas will be at the pressure of from about 3 to about 100 atmospheres.

Preferably the vent gas will be at a pressure from about 5 to 30 atmospheres and typically at from about 14 to 27 atmospheres. In contrast the pressure on the permeated gas stream typically found in the bores of the hollow fiber membranes can range as low as 1 to 95 atmospheres, preferably from about 3 to about 27 atmospheres and typically from about 5 to about 25 atmospheres. Thus the differential pressure maintained between the vent gas stream contacting the non-permeate side of the hollow fiber membrane and the permeated stream generated on the opposite side of the membranes may range from as low as about 2 to as high as about 100 atmospheres, depending upon the inherent strength and resistance to rupture of the hollow fiber membranes employed. Preferably such differential will range from about 2 to about 40 atmospheres, and most typically from about 10 to about 25 atmospheres. Sufficient effective membrane surface area and pressure differential is provided that at least about 40% and preferably from about 65 to 98% of the hydrogen in the vent gas stream permeates the separation membrane. The vent gas stream will also generally be at a temperature of from about 10° to about 60° C. and preferably at from about 20° to about 50° C.

In the present invention the separation vessel contains membranes in hollow fiber form with a plurality of the hollow fiber membranes arranged substantially parallel in bundle form. The vent gas stream can be contacted on either the outside or inside surface of the hollow fiber membrane but is preferably contacted on the outside or shell side surface thereof. Either radial or axial flow on and about the hollow fiber membranes can be established. The non-permeated gas mixture or shell side effluent from the separator can be within 0.1 to 3 atmospheres of the pressure of the vent gas stream fed to the separator, i.e. very little pressure drop is experienced on the shell side of the hollow fiber membranes in either radial or axial flow. If axial flow is employed, the present process is found to be advantageous either in concurrent or countercurrent mode, although it is most preferred to operate in a countercurrent manner. Thus by establishing countercurrent flow by admitting the vent gas stream at the end of a hollow fiber membrane separator at which the bore effluent or permeated stream is removed an increased hydrogen partial pressure differential across the hollow fiber membranes is maintained since the concentration of hydrogen increases in the bore as it flows in the direction in which the higher concentration of hydrogen is present in the vent gas stream.

The separator containing the hollow fiber separation membranes may be of any suitable design for gas separation providing either bore side feed or, more preferably, shell side radial or axial flow about the hollow fiber membranes. The separator vessel may be either single or double ended radial flow design where the vent gas stream is admitted to a gas feed conduit positioned at the center of the hollow fiber membrane bundle, the permeated gas stream is withdrawn from the bores of the hollow fiber at either one or both ends of the vessel, and the non-permeated gas is removed from either one or both ends of the shell side of the separator vessel. For use of shell side axial flow the separator vessel may be of double ended design wherein the vent gas stream is admitted in the mid portion of the shell of the separator vessel and the non-permeated gas removed from both ends of the shell while the permeated gas stream may be removed from the bores of the hollow fibers at either one or both ends of the separator vessel. Preferably the separator vessel is of single ended design in which the permeated gas from the bores is removed from one end only and the non-permeated gas can be removed from either end of the separator vessel, while the vent gas can be admitted to the separator vessel at any point from one end to the opposite end of the shell. In order to establish the most desirable countercurrent flow it is preferable to admit the vent gas at the same end of the separator at which the permeated gas is removed and to remove the non-permeated gas from the opposite end of the separator.

Any suitable material selectively permeable to hydrogen, and desirably carbon dioxide, in favor of carbon monoxide and other gases may be employed for the hollow fiber separation membrane. Suitable membrane materials include the metallic and inorganic membranes previously mentioned as well as organic polymers or organic polymers mixed with inorganics such as fillers, reinforcements and the like. Typical organic polymers which are suitable for the formation of hollow fiber separation membranes can be substituted or unsubstituted polymers and may be selected from polysulfones; polystyrenes, including styrene-containing polymers such as acrylonitrile-styrene copolymers, styrene-butadiene copolymers and styrene-vinylbenzyl halide copolymers; polycarbonates; cellulosic polymers, such as cellulose acetate, cellulose acetate-butyrate, cellulose propionate, ethyl cellulose, methyl cellulose, nitro cellulose, etc.; polyamides and polyimides, including aryl polyamides and aryl polyimides; polyethers, polyarylene oxides, such as polyphenylene oxide and polyxylylene oxide; polyesteramidediisocyanates; polyurethanes; polyesters, including polyacrylates, such as polyethylene terephthalate, polyalkyl methacrylates, polyalkyl acrylates, polyphenylene terephthalate, etc.; polysulfides; polymers from monomers having α-olefinic unsaturation other than mentioned above such as polyethylene, polypropylene, polybutene-1, poly-4-methylbenzene-1, polyvinyls, e.g. polyvinylchloride, polyvinylfluoride, polyvinylidene chloride, polyvinylidene fluoride, polyvinyl alcohol, polyvinyl esters such as polyvinyl acetate and polyvinyl propionate, polyvinyl pyridines, polyvinyl pyrrolidones, polyvinyl ethers, polyvinyl ketones, polyvinyl aldehydes such as polyvinyl formal and polyvinyl butyral, polyvinyl amines, polyvinyl phosphates and polyvinyl sulfates; polyallyls; polytriazoles; polybenzimidazoles; polycarbodiimides; polyphosphazines; etc., and interpolymers including block interpolymers containing repeating units from the above such as terpolymers of acrylonitrile-vinylbromidesodium salt of p-sulfophenylmethallyl ether; and grafts and blends containing any of the foregoing. Typical substituents providing substituted polymers include halogens such as fluorine, chlorine and bromine; hydroxyl groups; lower alkyl groups; lower alkoxy groups; monocyclic aryl; lower acyl groups and the like.

The hollow fiber membrane material is preferably as thin as possible in order to improve the rate of permeation through the membrane, yet of sufficient thickness to insure adequate strength to the hollow fiber membrane to withstand the separation conditions, including differential pressures and differential partial pressures employed. Hollow fiber membranes may be isotropic, i.e. have substantially the same density throughout, or they may be anisotropic, i.e. having at least one zone of greater density than at least one other zone of the fiber membranes. The hollow fiber membranes may be chemically homogeneous, i.e. constructed of the same material, or they may be composite membranes. Suitable composite membranes may comprise a thin layer which effects the separation on a porous physical support which provides the necessary strength to the hollow fiber membrane to withstand the separations. Other suitable composite hollow fiber membranes are the multicomponent hollow fiber membranes disclosed by Henis et al in Belgian Pat. No. 860,811 published May 16, 1978 and herein incorporated by reference. These membranes comprise a porous separation membrane which substantially effects the separation and a coating material in occluding contact with the porous separation membrane. These multicomponent membranes are particularly attractive for gas separations including those separating hydrogen and carbon dioxide from carbon monoxide, nitrogen and other gases, in that good selectivity for separation and high flux through the membrane can be obtained.

The materials for coating of these multicomponent membranes may be natural or synthetic substances, and are often polymers, which advantageously exhibit the appropriate properties to provide occluding contact with the porous separation membrane. Synthetic substances include both addition and condensation polymers. Typical of the useful materials which can comprise the coating are polymers which can be substituted or unsubstituted and which are solid or liquid under gas separation conditions, and include synthetic rubbers; natural rubbers; relatively high molecular weight and/or high boiling liquids; organic prepolymers; polysiloxanes; silicone polymers; polysilazanes; polyurethanes; polyepichlorohydrins; polyamines; polyimines; polyamides including polylactams; acrylonitrile-containing copolymers such as poly(α-chloroacrylonitrile) copolymers; polyesters including polyacrylates e.g. polyalkyl acrylates and polyalkyl methacrylates, wherein the alkyl groups have from 1 to about 8 carbon atoms, polysebacates, polysuccinates, and alkyd resins; terpinoid resins; linseed oil; cellulosic polymers; polysulfones, especially aliphatic-containing polysulfones; polyalkylene glycols such as polyethylene glycol, polypropylene glycol, etc.; polyalkylene polysulfates; polypyrrolidones; polymers from monomers having α-olefinic unsaturation such as polyolefins, e.g. polyethylene, polypropylene, polybutadiene, poly(2,3-dichlorobutadienes), polyisoprene, polychloroprene, polystyrene, including polystyrene copolymers, e.g. styrenebutadiene copolymers, polyvinyls such as polyvinyl alcohol, polyvinyl aldehydes, e.g. polyvinyl formal and polyvinyl butyral, polyvinyl ketones, e.g. polymethylvinyl ketone, polyvinyl esters, e.g. polyvinyl benzoates, polyvinyl halides, e.g. polyvinyl bromide, polyvinylidene halides, polyvinylidene carbonates, poly(N-vinylmaleamide), etc., poly(1,5-cyclooctadiene), poly(methylisopropenyl ketone), fluorinated ethylene copolymers, polyarylene oxides, e.g. polyxylylene oxides; polycarbonates; polyphosphates, e.g. polyethylene methyl phosphate; and the like, and any interpolymers including the interpolymers containing repeating units from the above, and grafts and blends containing any of the foregoing. The polymers may or may not be polymerized after application to the porous separation membrane.

In the present process the desired recovered non-permeated gas stream comprising those gases which do not permeate through the hollow fiber membranes is preferably withdrawn from the outside or shell side of such membranes for reasons of economy of recompression and efficiency of gas separation. This non-permeated gas mixture has a much enhanced proportion of carbon monoxide with substantial proportions of the hydrogen and carbon dioxide previously present now excluded from such stream. It has been found that despite substantial variation in the mole percentages of carbon monoxide contained in the vent gas stream the non-permeated gas stream is comprised of at least 85 mole percent and often greater than 90 mole percent of carbon monoxide, the desired recovered reactant.

Control of the differential pressures between the vent gas stream contacting one side of the hollow fiber membrane and the permeated gas stream generated on the second side thereof may be achieved by any convenient method. One suitable method of such control involves adjusting the pressures maintained by the pressure control valves in the respective streams. Total flows of the respective streams can also be controlled by means of flow control valves. In order to minimize recompression and the expense thereof, one very suitable method to control such differential pressures will involve establishing a minimum pressure required in the permeated gas stream for its forwarding to vent or flare and varying by means of a pressure controller on the vent gas feed stream from a pressure just sufficient to establish permeation across the membranes up to the pressure at which the vent gas stream leaves the last pretreatment prior to passing to the membrane permeator, such as a solid adsorbent bed or a liquid absorbent scrubber. During operation of the process, if the total flow of vent gas is for some reason diminished, adjustment can be made by restricting the flow of the non-permeated gas stream, or by varying the total surface area of membranes contacted by cutting out one or more parallel membrane permeator vessels without the necessity of changing the pressures imposed on each stream or the pressure differential between them. Other suitable means of control which can be employed if desired, include control to a specific content of one or more of the desired gases in the non-permeated gas stream as determined by analysis for such gas or gases and effected by varying pressure differentials, flow rates and/or total membrane surface areas.

The following examples are provided to further illustrate the invention. All parts of percentages of gases are by weight unless otherwise indicated.

EXAMPLE I

A vent gas from an acetic acid carbonylation reactor which had been cooled, condensable liquids separated therefrom and passed through a tower absorber in contact with crude acetic acid liquid was split into two portions. A small slip stream of the vent gas at approximately 28.2 atmospheres and 50° C. was passed to a liquid trap at approximately 30° C. to remove any liquid condensed by the line cooling of approximately 20° C. Then the gas was passed through two beds in series of activated carbon adsorbent to assure removal of acetic acid vapors. From the carbon beds the gas was passed through a permeator for separation of a part of the hydrogen and carbon dioxide content. The permeator contained poly(siloxane)-coated anisotropic polysulfone hollow fiber membranes prepared substantially in accordance with the method disclosed in Example 64 of Belgian Pat. No. 860,811 issued May 16, 1978 of Henis et al. The polysulfone had a molecular weight in excess of 10,000 and the poly(siloxane) a molecular weight in excess of 1,000 prior to crosslinking same. The polysulfone hollow fiber membranes coated on the outer surface with poly(siloxane) had an inside diameter of approximately 250 microns, an outside diameter of approximately 500 microns and a wall thickness of approximately 125 microns. The membranes in the permeator had a effective surface area of approximately 5500 square centimeters. The gas was contacted with the outer surfaces of the membranes in axial flow, the non-permeated gas stream withdrawn from the opposite end of the permeator shell and the permeated gas stream from the bores of the hollow fibers at the end of the permeator at which the vent gas was fed.

Prior to placing on stream, after one week and after 3 months of operation on the vent gas stream the hollow fiber permeator was tested with each of hydrogen and carbon monoxide gases separately, and the results are set out in Table 1A below.

TABLE 1A

| Gas | Permeabilities, P/1 × 10⁶ | | |
|---|---|---|---|
| | Initial | 1 week | 3 months |
| Hydrogen | 60 | 58.5 | 55.6 |
| Carbon Monoxide | 2.5 | — | 2.23 |
| S.F.$_{CO}^{H_2}$ | | | |

It is apparent that there was essentially no change in performance of the permeator over a period of three months of operation on the vent gas stream.

The initial permeabilities of the gas comprising the vent gas stream were determined at a temperature of approximately 30° C., a pressure differential of 24.5 atmospheres, i.e. 28.2 atmospheres pressure on the vent gas feed and 3.7 atmospheres pressure on the permeated gas stream, and flow rates of 10,770 cc/min STP for the vent gas stream and 2370 cc/min for the permeated gas stream. The composition of the vent gas stream, and the permeabilities and separation factor for hydrogen in respect to carbon monoxide and set out in Table 1B. It was concluded that the contact of the stream of relatively low hydrogen content, i.e. 15.2 mol % hydrogen, was inefficient due to rapid depletion of the hydrogen content of the non-permeated stream. This accounted for the somewhat lower hydrogen permeability found with the mixed vent gas stream than with the pure gas.

TABLE 1B

| Vent Stream Gas Permeabilities | |
|---|---|
| Feed Composition, Mol % | Permeabilities, P/1 × 10⁶ |
| Hydrogen 15.16 | 35.1 |
| Carbon Dioxide 2.18 | 15.0 |
| Carbon Monoxide 76.30 | 2.19 |
| Methane 0.97 | 1.53 |
| Nitrogen 5.39 | 1.89 |
| S.F. $\frac{H_2}{CO}$ | 16.0 |

EXAMPLE II

An acetic acid synthesis process is operated at steady state conditions with a total vent gas withdrawal of 228 kg/hr (503 lbs/hr) and the composition of the vent gas determined. The compositions of a non-permeated recovered carbon monoxide-rich gas stream and of a permeated, vented gas stream were determined based upon computer calculations employing a membrane separation unit composed of identical hollow fiber membranes to those described in Example I. The unit comprises two parallel gas permeators each having a surface area of approximately 93 square meters for a total surface area of approximately 186 square meters. The vent gas stream which has been freed of condensable liquids and contacted with crude acetic acid is first passed through a bed of activated carbon at approximately 37° C. and then through the gas permeator at the same temperature. The compositions of the vent gas stream prior to passage through the carbon bed, and the non-permeated gas stream and permeated gas stream exiting the permeator are set out in Table II below.

TABLE II

| | Compositions of Gas Streams, kg/hr. | | |
|---|---|---|---|
| | Vent Gas, 28.2 atm. | Non-Permeated Gas, 28.1 atm. | Permeated Gas, 2.72 atm. |
| $H_2$ | 2.63 | .68 | 1.95 |
| CO | 199.8 | 179.9 | 19.9 |
| $CO_2$ | 6.98 | 1.58 | 5.4 |
| $N_2$ | 17.52 | 15.8 | 1.77 |
| $CH_4$ | .63 | .59 | .04 |
| AcOH | .68 | — | — |

EXAMPLE III

A propionic acid synthesis process is operated at steady state conditions with a total vent gas of known composition withdrawn at the rate of 33.6 kg. (74.24 lbs.) per 454 kg. of propionic acid. The vent gas is treated in the same manner as in Example II to generate a non-permeated gas stream suitable for recycle and a permeated gas stream for venting. The compositions of each of the streams are determined based upon computer calculations employing one of the gas permeators described in Example II with a total surface area of 93 square meters. The vent gas stream which has been freed of condensable liquids and contacted with crude propionic acid is first passed through a bed of activated carbon and then through the gas permeator. The compositions of the vent gas stream, the non-permeated gas stream and the permeated gas stream are set out in Table III below.

TABLE III

| | Composition of Gas Streams, kgs/454 kg of product | | |
|---|---|---|---|
| | Vent Gas | Non-Permeated Gas | Permeated Gas |
| CO | 11.8 | 10.68 | 1.17 |
| $CO_2$ | 11.1 | .045 | 11.05 |
| $H_2$ | .458 | .045 | .413 |
| $C_2H_4$ | 8.24 | 7.7 | .544 |
| $C_2H_6$ | .725 | .653 | .072 |
| $N_2$ | .96 | .82 | .14 |
| PrOH | .33 | — | — |

EXAMPLE IV

An acetic acid synthesis process is operated at steady state conditions with a total vent gas withdrawal of 440 kg/hr. (969.7 lbs/hr.) and the composition of the vent gas determined. The compositions of a non-permeated carbon monoxide-rich gas stream and of a permeated, vented gas stream were determined based upon computer calculations. In this instance the CO-rich recovered gas is heated to 160° C. by passing through a heat exchanger against 90 kg. steam and then directed to one of two activated carbon beds of approximately 0.53 cubic meters each to remove deposited acetic acid and regenerate same. The beds are regenerated with heated non-permeated gas for 12 hours and then cooled with non-permeated gas at 30° C. for 12 hours, each bed being regenerated on a 24 hour cycle. The membrane separator unit comprises two permeators in parallel each of 93 square meters surface area and containing the same hollow fiber membranes as described in Example I. The composition of the vent gas, the non-permeated gas, the permeated gas and the heated recovered gas recycled at 30.6 atmospheres pressure from the carbon beds are set out in Table IV below.

TABLE IV

| | Gas Compositions, Kgs/hr. | | | |
|---|---|---|---|---|
| | Vent Gas, 28.2 atm. | Non-Permeated Gas, 27.2 atm. | Permeated Gas, 2.7 atm. | Recycled Gas, 30.6 atm. |
| $H_2$ | 5.47 | 1.64 | 3.83 | 1.64 |
| CO | 383 | 345 | 38.3 | 345 |
| $CO_2$ | 13.6 | 3.18 | 10.42 | 3.18 |
| $N_2$ | 34.5 | 32.9 | 1.64 | 32.9 |
| $CH_4$ | 1.231 | 1.227 | 0.04 | 1.23 |
| AcOH | 1.81 | — | — | 3.62 |

It is apparent that substantially all of the acetic acid which had previously been vented can be recovered from the carbon beds by regenerating the beds by the heated carbon monoxide gas stream.

EXAMPLE V

An acetic acid synthesis process is operated in the same manner as in Example II with the exception that the vent gas stream freed of condensable liquids and contacted with crude acetic acid is scrubbed with liquid methanol in a tower scrubber. The vent gas exiting the scrubber is reduced in pressure from 28.2 atmospheres to 21.4 atmospheres prior to contacting the hollow fiber membrane permeator having a surface area of approximately 93 square meters. The hollow fiber membranes comprising the permeator are of the same general type and composition as described in Example I with the exception that the inside diameter is approximately 120 microns, the outside diameter approximately 450 microns and the wall thickness approximately 165 microns. The approximate compositions of the vent gas stream, the non-permeated gas stream and the permeated gas stream determined by computer calculations are set out in Table V below.

TABLE V

| | Composition of Gas Streams, kg/hr | | |
|---|---|---|---|
| | Vent Gas 21.4 atm. | Non-permeated Gas 21.1 atm. | Permeated Gas 1.2 atm. |
| $H_2$ | 1.96 | .04 | 1.92 |
| CO | 93.2 | 70.0 | 23.2 |
| $CO_2$ | 3.16 | .91 | 2.24 |
| $CH_4$ | .153 | .134 | .018 |
| $N_2$ | 9.10 | 8.30 | 0.80 |
| $CH_3OH$ | .159 | .014 | .145 |

Thus, scrubbing with methanol is also a useful way of rendering the vent gas stream non-degrading to the membranes when saturation with methanol vapor in the scrubbed gas stream is avoided.

What is claimed is:

1. In a continuous homogeneous catalytic carbonylation process wherein at least one reactant selected from the group consisting of an olefin, an alcohol, an ester derivative of said alcohol, a halide derivative of said alcohol or an ether derivative of said alcohol is reacted with carbon monoxide in liquid phase in a carbonylation reactor and in the presence of a catalyst system that contains (a) a rhodium or iridium component, and (b) an iodine or bromine component, and wherein a mixed gas stream is removed from the carbonylation reactor, condensable liquids separated therefrom and said gas stream vented, the improvement comprising contacting said vent gas stream with a plurality of organic polymeric hollow fiber membranes potentially degraded by carbonylation products and selectively permeable to hydrogen under conditions substantially non-degrading of said membranes, said conditions comprising said vent gas stream substantially free of carbonylation product and alkyl halide, to generate a non-permeated gas stream of higher carbon monoxide content than said vent gas stream and a permeated stream relatively lower in carbon monoxide content than said vent gas stream, and recycling said non-permeated gas stream of increased carbon monoxide content to said carbonylation reactor.

2. The process of claim 1 wherein the hollow fiber membranes comprise porous separation membranes comprising polysulfone.

3. The process of claim 1 wherein the hollow fiber membranes comprise multicomponent hollow fiber membranes comprising a polysulfone porous separation membrane and a poly(siloxane) coating material in occluding contact with the outer surface thereof.

4. The process of claim 1 wherein carbonylation product in the vent gas is adsorbed onto a solid adsorbent prior to said contacting.

5. The process of claim 4 wherein the solid adsorbent is activated carbon.

6. The process of claim 1 wherein carbonylation product in the vent gas is absorbed in a liquid absorbent prior to said contacting.

7. The process of claim 6 wherein the liquid absorbent is methanol.

8. The process of claim 6 wherein the liquid absorbent is water.

9. The process of claim 1 wherein the improvement comprises in addition the recovery of the carbonylation product in said vent gas prior to said contacting and recycling such carbonylation product to said carbonylation process.

10. The process of claim 9 wherein carbonylation product in said vent gas is recovered by adsorbing onto a solid adsorbent, the solid absorbent is regenerated with at least a portion of an essentially carbon monoxide gas stream and said regenerating gas stream is thereafter passed to the carbonylation reactor.

11. The process of claim 10 wherein the regenerating gas stream is carbon monoxide feed stream.

12. The process of claim 10 wherein the regenerating gas stream is said non-permeated gas stream.

13. The process of claim 10 wherein the solid adsorbent is selected from the group consisting of activated carbon, silica, bauxite and alumina.

14. The process of claim 10 wherein the solid adsorbent is activated carbon.

15. The process of claim 9 wherein carbonylation product in said vent gas is recovered by absorbing in a liquid absorbent, and at least a portion of said liquid absorbent containing carbonylation product is returned to the carbonylation process.

16. The process of claim 15 wherein the liquid absorbent is selected from the group consisting of alkanols and water.

17. The process of claim 15 wherein the liquid absorbent is methanol.

18. The process of claim 15 wherein the liquid absorbent is water.

19. In a continuous homogeneous catalytic carbonylation process for the production of acetic acid wherein at least one reactant selected from the group consisting of methanol, an ester derivative of methanol, a halide derivative of methanol or an ether derivative of methanol is reacted with carbon monoxide in liquid phase in a carbonylation reactor and in the presence of a catalyst system that contains (a) a rhodium or iridium component, and (b) an iodine or bromine component, and wherein a mixed gas stream is removed from the carbonylation reactor, condensable liquids separated therefrom and said gas stream vented, the improvement comprising contacting said vent gas stream with a plurality of organic polymeric hollow fiber membranes potentially degraded by acetic acid and selectively permeable to hydrogen under conditions substantially non-degrading of said membranes, said conditions comprising said vent gas stream substantially free of acetic acid and methyl halide, to generate a non-permeated gas stream of higher carbon monoxide content than said vent gas stream and a permeated gas stream relatively lower in carbon monoxide content than said vent gas stream, and recycling said non-permeated gas stream of increased carbon monoxide content to said carbonylation reactor.

20. The process of claim 19 wherein said acetic acid in the vent gas is adsorbed onto a solid adsorbent or absorbed in a liquid absorbent prior to said contacting.

21. The process of claim 20 wherein said solid adsorbent is selected from the group consisting of activated carbon, silica, bauxite and alumina.

22. The process of claim 20 wherein said liquid absorbent is selected from the group consisting of methanol and water.

23. The process of claim 19 wherein the improvement comprises in addition the recovery of the acetic acid in said vent gas prior to said contacting and recycling said acetic acid to said acetic acid process.

24. The process of claim 23 wherein the acetic acid in the vent gas is recovered by adsorbing onto a solid adsorbent, the solid adsorbent is regenerated with at least a portion of an essentially carbon monoxide gas stream and said regenerating gas stream is thereafter passed to the carbonylation reactor.

25. The process of claim 24 wherein the solid adsorbent is selected from the group consisting of activated carbon, silica, bauxite and alumina.

26. The process of claim 24 wherein the solid adsorbent is activated carbon.

27. The process of claim 23 wherein acetic acid in the vent gas is recovered by absorbing in a liquid absorbent and at least a portion of said liquid absorbent is returned to the acetic acid process.

28. The process of claim 27 wherein the liquid absorbent is selected from the group consisting of methanol and water.

29. The process of claim 27 wherein the liquid absorbent is methanol.

30. The process of claim 27 wherein the liquid absorbent is water.

* * * * *